United States Patent
Nübling et al.

(10) Patent No.: US 6,465,223 B1
(45) Date of Patent: Oct. 15, 2002

(54) ENZYME-CATALYZED RACEMIC CLEAVAGE OF PRIMARY AMINES

(75) Inventors: Christoph Nübling, Hassloch; Klaus Ditrich, Gönnheim; Christian Dully, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/762,326

(22) PCT Filed: Aug. 13, 1999

(86) PCT No.: PCT/EP99/05958

§ 371 (c)(1),
(2), (4) Date: Feb. 6, 2001

(87) PCT Pub. No.: WO00/11203

PCT Pub. Date: Mar. 2, 2000

(30) Foreign Application Priority Data

Aug. 20, 1998 (DE) .......................................... 198 37 745

(51) Int. Cl.[7] .............................. C12P 13/00; C12N 9/20
(52) U.S. Cl. ........................ 435/128; 435/198; 435/280
(58) Field of Search ................................ 435/128, 198, 435/280

(56) References Cited

U.S. PATENT DOCUMENTS

| | | | |
|---|---|---|---|
| 5,728,876 A | | 3/1998 | Balkenhohl et al. .......... 564/136 |
| 5,981,267 A | * | 11/1999 | Wong et al. |
| 6,063,615 A | * | 5/2000 | Sturmer et al. |
| 6,068,996 A | * | 5/2000 | Dreisbach et al. |
| 6,187,582 B1 | * | 2/2001 | Stelzer |
| 6,214,608 B1 | * | 4/2001 | Balkenhohl et al. |
| 6,214,609 B1 | * | 4/2001 | Landis et al |

FOREIGN PATENT DOCUMENTS

| | | | |
|---|---|---|---|
| DE | 19637336 A1 | * | 6/1994 |
| EP | 890 649 | | 1/1999 |
| WO | WO-9623894 A1 | * | 8/1996 |
| WO | WO 97/28271 | | 8/1997 |
| WO | WO-97/46698 A1 | * | 12/1997 |

OTHER PUBLICATIONS

Orsat et al. "Homocarbons as Substrates for the Enantioselective Enzymatic Protection of Amines" J. Am. Chem Soc. vol. 118 (1996) pp. 712–713.

Sanchez et al. "Candida Antarctica lipase catalyzed resolution of ethyl(±)–3–aminobytyrate" Tetrahedron Asymetry vol. 8, (1997) pp. 37–40.

\* cited by examiner

*Primary Examiner*—Herbert J. Lilling
(74) *Attorney, Agent, or Firm*—Keil & Weinkauf

(57) ABSTRACT

The present invention relates to a process for resolving racemates of alkoxy-substituted primary amines by reacting with an ester in the presence of a lipase and subsequently separating the optically active amide which is formed from the unreacted optically active amine. This is followed where appropriate by hydrolysis of the optically active amide, separation of the optically active amine produced thereby from the acid from which the ester is derived, racemization and recycling of the unwanted enantiomer of the amine, and esterification and recycling of the acid.

14 Claims, No Drawings

ENZYME-CATALYZED RACEMIC CLEAVAGE OF PRIMARY AMINES

The present invention relates to a process for resolving racemates of alkoxy-substituted primary amines by reacting with an ester in the presence of a lipase and subsequently separating the optically active amide which is formed from the unreacted optically active amine. This is followed where appropriate by hydrolysis of the optically active amide, separation of the optically active amine produced thereby from the acid from which the ester is derived, racemization and recycling of the unwanted enantiomer of the amine, and esterification and recycling of the acid.

WO95/08636 describes a process for resolving racemates of primary and secondary amines by reacting w with an ester in the presence of hydrolases, especially lipases. The preferred amines are primary arylalkylamines. WO 96/23894 describes a process for resolving racemates of primary and secondary heteroatom-substituted amines by reacting with an ester in the presence of hydrolases, especially lipases. The preferred amines are O-protected amino alcohols. The preferred esters mentioned in both applications are the $C_{1-4}$-alkyl esters Of $C_{1-4}$-alkoxyacetic acids.

DE 196 03 575 and DE 196 37 336 describe a process for preparing optically active amines by reacting the corresponding racemates with an ester in the presence of lipase from Candida antarctica. The preferred amines are alkoxy-substituted alkylamines, especially 2-amino-1-methoxypropane, and substituted phenylethylamines, especially 4-chlorophenylethylamine. The e preferred esters are $C_{1-6}$-alkanoic esters and $C_{1-8}$-alkoxyalkanoic esters, especially methyl methoxyacetate. Finally, DE 196 21 686 describes a process for preparing optically active amines by reacting the corresponding racemates with an ester in the presence of hydrolases, in which substituted phenylethylamines, especially 4-chlorophenylethylamine, and $C_{1-4}$-haloalkanoic esters, especially ethyl chloroacetate, are preferred.

It has now been found, surprisingly, that the process described at the outset can be carried out particularly advantageously if esters with long-chain alcohol residues are used.

The process for resolving racemates of amines takes place particularly advantageously if an ester of the general formula 1

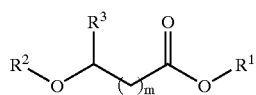

in which m is 0 or 1, $R^1$ is branched or unbranched $C_6$–$C_{20}$-alkyl or heteroalkyl having 6 to 20 backbone atoms, $R^2$ is $C_1$–$C_8$-alkyl or phenyl, $R^3$ is H or $C_1$–$C_4$-alkyl, is reacted with an alkoxy or benzyloxy substituted primary amine of the general formula 2

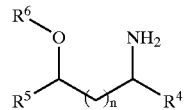

in which n is 0 or 1, $R^4$, $R^5$ are, independently of one another, H, $C_1$–$C_8$-alkyl or phenyl, $R^6$ is $C_1$–$C_6$-alkyl or benzyl, in the presence of a lipase, resulting in amides of the general formula 3

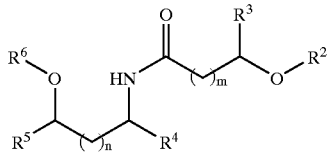

in which n, m, $R^2$, $R^3$, $R^4$, $R^5$ and $R^6$ have the meanings stated above, which comprise an excess of one optical isomer of the amide.

There is preferably formation of an (R) amide, and particularly preferably enantioselective acylation with a high enantiomeric excess of more than 50% ee, in particular more than 80% ee, especially more than 90% ee. The unreacted amine comprises an excess of (S) amine, preferably more than 50% ee, in particular more than 90% ee, especially more than 99% ee. (R) amide or (R) amine mean the optically active amines or amides having the (R) configuration at the carbon of the amino group. An analogous statement applies to (S) amine or (S) amide.

It has additionally been found that it is advantageous to dry the starting materials. This can in principle take place in any manner known to the skilled worker, e.g. by azeotropic drying or through desiccants such as sodium sulfate, magnesium sulfate, KOH, phosphorus pentoxide, molecular sieves, silica gel or alumina.

It has additionally been found that it is advantageous to use acid-free starting materials. Acids can in principle be removed in any way known to the skilled worker, e.g. by extraction or distillation, where appropriate after previous neutralization with alkali metal or alkaline earth metal hydroxides such as sodium, potassium or calciuit hydroxide, with amines such as triethylamine, tributylamine, triethanolamine, pyridine or N,N-dimethylaniline, with carbonates such as sodium, potassium or calcium carbonate or with ion exchangers.

It is possible to use a large number of lipases in the process according to the invention. Microbial lipases from bacteria are preferred, such as lipases from the genera Bacillus or Pseudomonas, e.g. Amano P or the lipase from Pseudomonas spec. DSM 8246, or from fungi such as Aspergillus, or yeasts such as Candida. Further preferred lipases are, for example, the lipases SP 523, SP 524, SP 525, SP 526 and Novozy® 435, which are obtained from fungi such as Humicola, Mucor or Candida antarctica and which are commercially available from Novo Nordisk. It is additionally possible to use the lipases Chirazyme L1, L2, L3, L4, L5, L6, L7 and L8 which are commercially obtainable from Boehringer Mannheim. The lipases can be used in native or immobilized form. The immobilized lipases can be icroencapsulated, emulsified with prepolymers and polymerized, crosslinked with bifunctional substances (oligomers, aldehydes etc.), or bound to inorganic or organic carrier materials such as Celites, Lewatit, zeolites, polysaccharides, polyamides or polystyrene resins. Particularly preferred lipases are Novozy® 435 and Chirazyme L2. The enzyme-catalyzed racemate resolution can be carried out both in protic or aprotic solvents and without solvent. Examples of suitable solvents are hydrocarbons such as hexane, cyclohexane or toluene, ethers such as diethyl ether, dioxane, methyl tert-butyl ether, tert-amyl methyl ether or THF, nitriles such as acetonitrile, butyronitrile, alcohols such as tert-butanol, 3-methyl-3-pentanol, and halogenated hydrocarbons such as methylene chloride.

The reaction with lipase generally takes place under atmospheric pressure, where appropriate under inert gas such as nitrogen or argon. However, it can also be carried out under elevated pressure.

The temperature for the reaction of ester with the racemic alkoxy-substituted amine is normally from 0 to 90° C., preferably from 10 to 60° C., particularly preferably from 20 to 50° C.

From 0.5 to 2.0 mol, preferably 0.5 to 1 mol, of ester are used per mole of racemic amine. The amount of enzyme required depends on the activity of the enzyme preparation and the reactivity of the amine and can easily be established by preliminary tests. As a rule, from 0.1 to 10% by weight, preferably 1 to 5% by weight, of the immobilized enzyme preparation (based on racemic amine) are used. Novozym® has an activity of about 7000 U/g in the esterification of lauric acid with 1-propanol.

The course of the reaction can easily be followed by conventional methods such as GC or HPLC. When the desired conversion is reached, the reaction is preferably stopped by removing the catalyst, for example by filtering off the (carrier-bound) enzyme. The reaction can also be stopped, for example, by adding enzyme-decomposing substances such as acids or alkalis or by heating. In a continuous procedure, the conversion can be controlled via the loading of the enzyme, i.e. the amount of amine pumped through the enzyme reactor per unit time. The process can preferably be carried out continuously, but it can also be carried out batchwise or semicontinuously.

The enzyme-catalyzed racemate resolution finally results in a mixture of the acylated amine enantiomer, the unreacted amine enantiomer, the alcohol liberated from the ester during the acylation and, possibly, ester employed in excess. Distillation and extraction processes are particularly suitable for separating this mixture. Thus, low-boiling amines can be distilled out of the reaction mixture directly. The amide can subsequently be separated from the alcohol and, where appropriate, ester by distillation or extraction and can then be hydrolyzed in a conventional way with either an acid or base, for example by boiling with sulfuric acid or sodium or potassium hydroxide solution, with racemization or else without racemization. The hydrolysis can be carried out under atmospheric pressure and, where appropriate, also at an elevated temperature under increased pressure to accelerate the reaction. The second amine enantiomer formed in the hydrolysis can be isolated by distillation or extraction, where appropriate after being liberated from the ammonium salt. The acid formed in the hydrolysis can be recovered, where appropriate after acidification of the hydrolysis solution and preferably by extraction. The acid can be esterified by conventional processes, for example azeotropically or by extraction, and returned to the racemate solution process.

If only one enantiomer of the amine is required, it is possible to racemize the other and return the racemate to the process. It is possible in this way theoretically to convert all the racemate into the required enantiomer. Such racemizations can be carried out, for example, under the same conditions as for preparing amines from alcohols or ketones ("reductive amination").

Esters of the formula 1

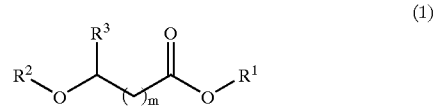

(1)

suitable for the process according to the invention are those in which m is 0 or 1, preferably 0

$R^1$ is branched or unbranched $C_6$–$C_{20}$-alkyl or heteroalkyl having 6 to 20 backbone atoms, it being possible for the alkyl or heteroalkyl radical to be substituted, independently of one another, by 1 to 5 halogen atoms, preferably F or Cl, and/or an oxo group. Heteroalkyl means that 1, 2 or 3 nonadjacent —$CH_2$— groups are replaced by —O—, —S—, —NH—, or 1 or 2 nonadjacent CH groups are replaced by N. Replacement of 1 or 2 $CH_2$ groups is preferred. The preferred heteroatom is O. Examples of $R^1$ are 1-hexyl, 2-hexyl, 3-hexyl, 2-methyl-1-pentyl, 3-methyl-1-pentyl, 4-methyl-1-pentyl, 2-methyl-3-pentyl, 2-ethyl-1-butyl, 1-heptyl, 2-heptyl-, 3-heptyl-, 2-methyl-1-hexyl, 3-methyl-1-hexyl, 2-ethyl-1-hexyl, 3-ethyl-1-hexyl, 2-methyl-1-heptyl, 3-methyl-1-heptyl, 1-octyl, 2-octyl-, 3-octyl-, 1-nonyl, 2-nonyl-, 3-nonyl, 1-decyl, 2-decyl, 3,7-dimethyl-1-octyl, 1-undecyl, 1-dodecyl, 1-tridecyl, 1-tetradecyl, 1-pentadecyl, 1-hexadecyl, 1-heptadecyl and 1-octadecyl, 2-methoxyacetoxyethyl, 2-methoxyacetoxybutyl, 2-methoxyacetoxyhexyl, 2-methoxyacetoxydecyl, chloroacetoxybutyl, chloroacetoxyhexyl, chloroacetoxydecyl, trichloroacetoxybutyl, trichloroacetoxyhexyl, trichloroacetoxydecyl, with preference given to branched or unbranched $C_6$–$C_{18}$-alkyl or heteroalkyl having 6 to 18 backbone atoms, e.g. 1-hexyl, 1-heptyl, 2-ethyl-1-hexyl, 1-octyl, 1-decyl, 1-dodecyl, 1-tetradecyl, 1-hexadecyl and 1-octadecyl, 2-methoxyacetoxyethyl, 2-methoxyacetoxybutyl, 2-methoxyacetoxyhexyl, 2-methoxyacetoxydecyl, chloroacetoxybutyl, chloroacetoxyhexyl, chloroacetoxydecyl, and particular preference to branched or unbranched $C_6$–$C_{14}$-alkyl or heteroalkyl having 6–14 backbone atoms, e.g.: 1-hexyl, 2-ethyl-1-hexyl, 1-octyl, 1-decyl and 1-tetradecyl, 2-methoxyacetoxyethyl, 2-methoxyacetoxybutyl, 2-methoxyacetoxyhexyl, 2-methoxyacetoxydecyl.

$R^2$ is $C_1$–$C_8$-alkyl such as methyl, ethyl, 1-propyl, 2-propyl, 1-butyl, 2-butyl, 1-pentyl, 2-pentyl, 1-hexyl, 2-hexyl, 1-heptyl, 2-ethylhexyl and 1-octyl, preferably methyl, ethyl, 1-propyl, 2-propyl and 1-butyl, particularly preferably methyl and ethyl or phenyl, $R^3$ is H, $C_1$–$C_4$-alkyl such as methyl, ethyl, 1-propyl, 2-propyl and 1-butyl, preferably H, methyl and ethyl.

Examples of esters of the formula 1 which are mentioned are the following preferred compounds:

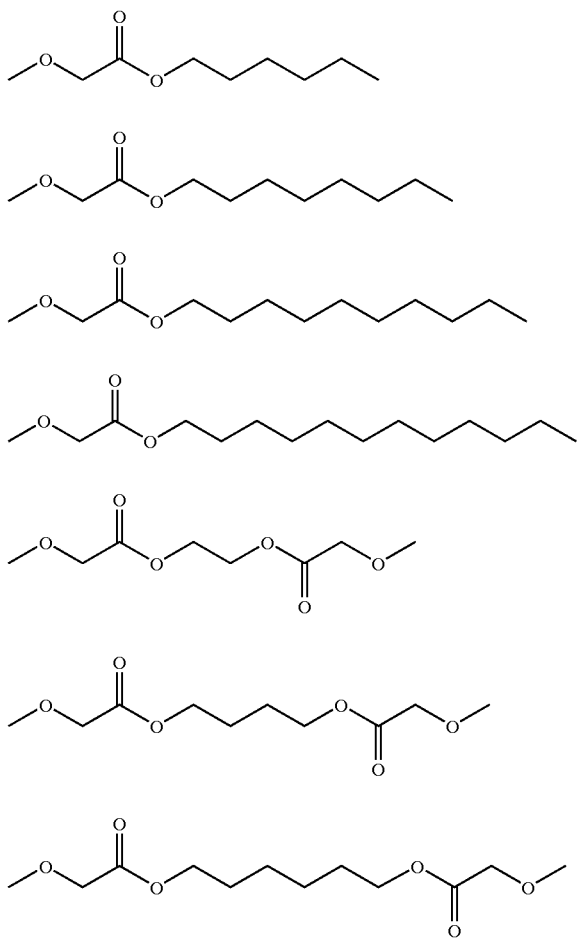

The process according to the invention is suitable for resolving racemates of alkoxy-substituted primary amines of the general formula 2

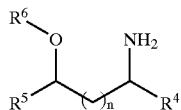

(2)

in which n is 0 or 1, preferably 0, $R^4$, $R^5$ are, independently of one another, H, $C_1$–$C_8$-alkyl such as methyl, ethyl, 1-propyl, 2-propyl, 1-butyl, 2-butyl, 1-pentyl, 2-pentyl, 1-hexyl, 2-hexyl, 1-heptyl, 2-ethylhexyl and 1-octyl or phenyl, preferably H, $C_1$–$C_4$-alkyl such as methyl, ethyl, 1-propyl, 2-propyl and 1-butyl, particularly preferably H, methyl and ethyl, $R^6$ is $C_1$–$C_6$-alkyl such as methyl, ethyl, 1-propyl, 2-propyl, 1-butyl, 2-butyl, 1-pentyl, 2-pentyl, 1-hexyl and 2-hexyl or benzyl, preferably methyl, ethyl and benzyl.

The following compound is mentioned as a preferred example of amines of the formula 2:

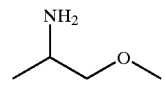

EXAMPLE 1

A mixture of 1 mole equivalent of 2-amino-1-methoxypropane and 1 mole (0.5 mole for diesters) equivalent of the particular methoxyacetic ester is mixed with 5% by weight (based on the amine) of Novozy® 435 and shaken at room temperature for 24 hours. The conversions were determined by gas chromatography and are compiled in Table 1:

TABLE 1

Comparison of the rates of acylation of 2-amino-1-methoxypropane with various methoxyacetic esters

| Time [h] | Methyl ester conversion [%] | Hexyl ester conversion [%] | Decyl ester conversion [%] | Ethanediol diester conversion [%] | 1,4-Butanediol diester conversion [%] |
|---|---|---|---|---|---|
| 0.25 | 17.5 | 19.3 | 14.5 | 26.4 | 20.4 |
| 0.5 | 21.7 | 31.1 | 26.0 | 30.5 | |
| 0.75 | 24.0 | 37.4 | 33.1 | 41.6 | 34.7 |
| 1 | 25.9 | 41.0 | 37.8 | 45.0 | 38.9 |
| 1.5 | 28.1 | 46.1 | 43.8 | 49.2 | 44.1 |
| 2 | 29.4 | 48.8 | 47.7 | 51.4 | 47.0 |
| 2.5 | 30.2 | 50.7 | 49.7 | 52.9 | 48.9 |
| 3 | 31.1 | 51.6 | 51.1 | 54.0 | 50.2 |
| 5 | 33.3 | 53.4 | 53.6 | 57.7 | 53.4 |
| 6 | 33.9 | 54.0 | 54.3 | 58.2 | 54.0 |
| 24 | 39.2 | 63.2 | 63.9 | 66.3 | 62.1 |

EXAMPLE 2

2 g of Novozy® 435 were introduced as a suspension in the particular ester into a glass tube (internal diameter: 1 cm) heated to 60° C. An equimolar mixture, which had been dried over molecular sieves (4 Å), of 2-amino-1-methoxypropane and the particular ester was then pumped at a constant rate through the enzyme bed. The conversions achieved thereby, and the enantiomeric excesses of the slower-reacting enantiomer [(S)-1-amino-2-methoxypropane] are compiled in Table 2:

TABLE 2

Comparison of the conversions and enantiomeric excesses on resolution of racemic 1-amino-2-methoxypropane with various methoxyacetic esters

| Ester | Loading [g/gh] | Conversion [%] | ee [%] |
|---|---|---|---|
| Methyl methoxyacetate | 7.5 | 3.1 | 3.0 |
| Isopropyl methoxyacetate | 7.5 | 54.9 | >99.5 |
| Isopropyl methoxyacetate | 25.0 | 41.1 | 64.0 |
| Decyl methoxyacetate | 25.0 | 61.5 | >99.5 |

(The loading corresponds to the amount of amine/ester mixture pumped through the enzyme bed per gram of Novozy® 435 and hour.)

We claim:

1. A process for preparing an optically active primary amine which comprises a) reacting a racemic primary amine with an ester (I) selected from the group consisting of

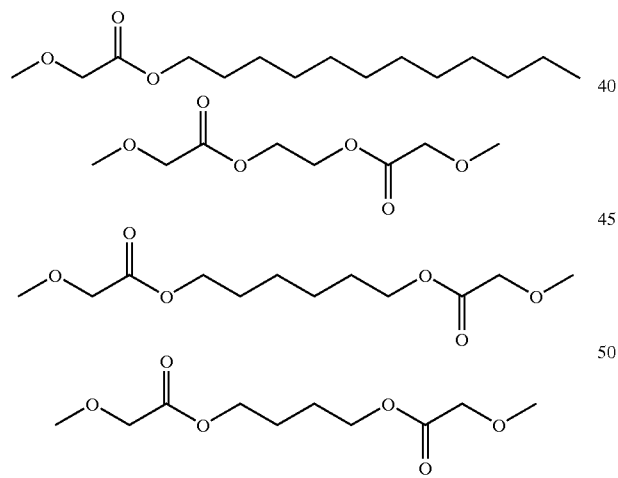

in the presence of a lipase to give a mixture comprising an enantioselectively acylated amine and residual primary amine in a first optically active form, and subsequently b) separating the acylated amine from residual primary amine, and, optionally, c) hydrolyzing the separated acylated amine to give a mixture comprising an acid corresponding to the ester (I) and the primary amine in a second optically active form.

2. A process for acylating a primary amine of formula 2

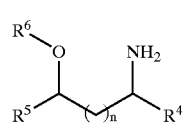
(2)

in which
n=0 or 1,
$R^4$, $R^5$=independently of one another H. $C_1$–$C_8$-alkyl or phenyl,
$R^6$=$C_1$–$C_6$-alkyl or benzyl,
which comprises reacting the primary amine with an ester (I) selected from the group consisting of

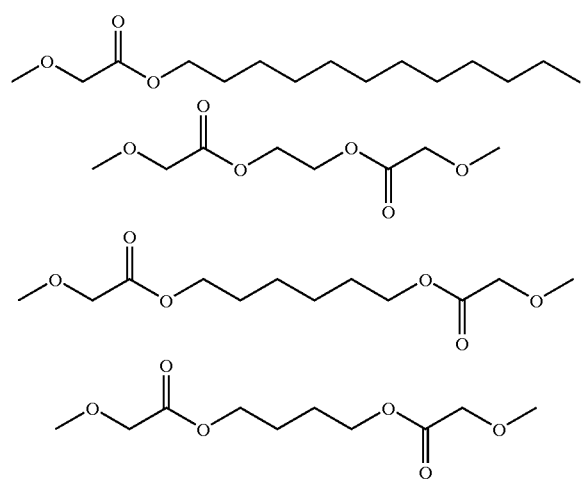

in the presence of a lipase.

3. The process of claim 1, wherein the primary amine is of formula 2

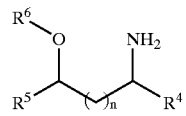
(2)

in which
n is 0 or 1, $R^4$, $R^5$ are, independently of one another, H, $C_1$–$C_8$-alkyl or phenyl, $R^6$ is $C_1$–$C_6$-alkyl or benzyl, and which comprises c) hydrolyzing the separated acylated amine to obtain a mixture comprising the amine in the second optically active form.

4. The process of claim 1, which further comprises racemizing the residual primary amine of the first optically active form and returning the racemized primary amine to stage (a) of the process.

5. The process of claim 1, wherein the acid obtained in stage (c) is esterified with dodecanol, ethyleneglycol, 1,4-butanediol or 1,6-hexanediol to give the ester (I), and (I) is turned to stage (a) of the process.

6. The process of claim 3, which further comprises racemizing the amine of the second optically active form and returning the racemized primary amine to stage (a) of the process.

7. The process of claim 3, wherein the acid obtained in stage (c) is esterified with methanol to give the ester (I), and (I) is returned to stage (a) of the process.

8. The process of claim 4, wherein the acid obtained in stage (c) is esterified with dodecanol, ethyleneglycol, 1,4-butanediol or 1,6-hexanediol to give the ester (I), and (I) is returned to stage (a) of the process.

9. A process for preparing an optically active primary amine which comprises a) reacting a racemic primary amine with an ester of formula (1)

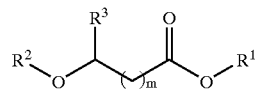

wherein m is 0;

$R^1$ is $C_6$–$C_{20}$-alkyl, or is group having 6 to 20 backbone atoms consisting of carbon members and 1 or 2 nonadjacent oxygen members, wherein one of said carbon members of said group optionally carries an oxo group;

$R^2$ is $C_1$–$C_8$-alkyl or phenyl;

$R^3$ is H or $C_1$–$C_4$-alkyl, in the presence of a lipase to give a mixture comprising an enantioselectively acylated amine and residual primary amine in a first optically active form, and subsequently b) separating the acylated amine from the residual primary amine, and, optionally, c) hydrolyzing the separated acylated amine to give a mixture comprising an acid corresponding to the ester of formula (1) and the primary amine in a second optically active form.

10. The process of claim 9, wherein the racemic primary amine is of formula (2)

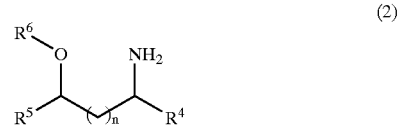

wherein n is 0 or 1;

$R^4$ and $R^5$ are independently of one another H, $C_1$–$C_8$-alkyl or phenyl;

$R^6$ is $C_1$–$C_6$-alkyl or benzyl.

11. The process of claim 9, which comprises hydrolyzing the separated acylated amine t obtain the mixture comprising the acid and the amine in the second optically active form.

12. The process of claim 11, which further comprises racemizing the residual primary amine Of the first optically active form and returning the racemized primary amine to stage (a) of the process.

13. The process of claim 11, wherein the acid is esterified with an alcohol $R^1OH$ to give the ester of formula (1), and the ester is returned to stage (a) of the process.

14. The process of claim 11, which further comprises racemizing the amine of the second optically active form and returning the racemized primary amine to stage (a) of the process.

* * * * *

UNITED STATES PATENT AND TRADEMARK OFFICE
CERTIFICATE OF CORRECTION

PATENT NO.    : 6,465,223 B1                                                                  Page 1 of 1
DATED         : October 15, 2002
INVENTOR(S)   : Nuebling et al.

It is certified that error appears in the above-identified patent and that said Letters Patent is hereby corrected as shown below:

Column 8,
Lines 48-50, "n is 0 or 1, $R^4$, $R^5$ are, independently of one another, H, $C_1$-$C_8$-alkyl or phenyl, $R^6$ is $C_1$-$C_6$-alkyl or benzyl, and which comprises" should be
--     n is 0 or 1,
       $R^4$, $R^5$ are, independently of one another, H, $C_1$-$C_8$-alkyl or phenyl,
       $R^6$ is $C_1$-$C_6$-alkyl or benzyl,
       and which comprises --.

Column 10,
Line 19, "t obtain" should be -- to obtain --.
Line 22, "Of" should be -- of --.

Signed and Sealed this

Seventh Day of January, 2003

JAMES E. ROGAN
*Director of the United States Patent and Trademark Office*